US010925569B2

(12) United States Patent
Ecabert et al.

(10) Patent No.: US 10,925,569 B2
(45) Date of Patent: Feb. 23, 2021

(54) DEVICE AND METHOD FOR CREATING A PANORAMIC X-RAY RECORDING USING A FIRST SEMI-TRANSPARENT X-RAY SCREEN AND A SECOND SEMI-TRANSPARENT X-RAY SCREEN

(71) Applicant: SIEMENS HEALTHCARE GMBH, Erlangen (DE)

(72) Inventors: Olivier Ecabert, Ebermannstadt (DE); Alexander Gemmel, Erlangen (DE); Gerhard Kleinszig, Forchheim (DE); Birgi Tamersoy, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 520 days.

(21) Appl. No.: 15/473,919

(22) Filed: Mar. 30, 2017

(65) Prior Publication Data
US 2017/0281109 A1   Oct. 5, 2017

(30) Foreign Application Priority Data

Mar. 30, 2016   (DE) .......................... 102016205176.8

(51) Int. Cl.
*A61B 6/00*  (2006.01)
*A61B 6/06*  (2006.01)
*A61B 6/04*  (2006.01)

(52) U.S. Cl.
CPC .............. *A61B 6/5241* (2013.01); *A61B 6/04* (2013.01); *A61B 6/0407* (2013.01);
(Continued)

(58) Field of Classification Search
CPC ........... A61B 6/06; A61B 6/52; A61B 6/5205; A61B 6/5235; A61B 6/5241; A61B 6/4035; A61B 6/4042; A61B 6/04; A61B 6/0407; A61B 6/0487; A61B 6/40; A61B 6/44; A61B 6/4429; A61B 6/4435; A61B 6/46;
(Continued)

(56) References Cited

U.S. PATENT DOCUMENTS 4,093,864 A * 6/1978 Hahn ....................... A61B 6/06
378/152
4,672,652 A * 6/1987 Hüttenrauch ............ A61B 6/06
378/148
(Continued)

FOREIGN PATENT DOCUMENTS

CN   101106659 A   1/2008
CN   101137018 A   3/2008
(Continued)

OTHER PUBLICATIONS

Rudin et al., "Region of interest fluoroscopy", Medical Physics 19 (5), Sep./Oct. 1992, pp. 1183-1189.
(Continued)

*Primary Examiner* — Allen C. Ho
(74) *Attorney, Agent, or Firm* — Laurence Greenberg; Werner Stemer; Ralph Locher

(57) ABSTRACT

During the generation of a panoramic x-ray recording, the use of semi-transparent x-ray screens allows the patient's x-ray exposure to be reduced when partial x-ray images are created, in spite of relatively large overlapping areas between the partial x-ray images.

10 Claims, 3 Drawing Sheets

(52) U.S. Cl.
CPC ............ *A61B 6/0487* (2020.08); *A61B 6/06* (2013.01); *A61B 6/40* (2013.01); *A61B 6/4035* (2013.01); *A61B 6/4042* (2013.01); *A61B 6/4085* (2013.01); *A61B 6/42* (2013.01); *A61B 6/4208* (2013.01); *A61B 6/4258* (2013.01); *A61B 6/44* (2013.01); *A61B 6/4429* (2013.01); *A61B 6/4435* (2013.01); *A61B 6/46* (2013.01); *A61B 6/461* (2013.01); *A61B 6/467* (2013.01); *A61B 6/469* (2013.01); *A61B 6/52* (2013.01); *A61B 6/5205* (2013.01); *A61B 6/5211* (2013.01); *A61B 6/5229* (2013.01); *A61B 6/5235* (2013.01); *A61B 6/54* (2013.01); *A61B 6/542* (2013.01); *A61B 6/544* (2013.01); *A61B 6/545* (2013.01)

(58) Field of Classification Search
CPC ......... A61B 6/461; A61B 6/467; A61B 6/469; A61B 6/5211; A61B 6/5229; A61B 6/54; A61B 6/542; A61B 6/544; A61B 6/545; A61B 6/42; A61B 6/4208; A61B 6/4258; G21K 1/02; G21K 1/025
USPC ................ 378/62, 63, 98.12, 147, 149–152, 378/156–159, 162, 165
See application file for complete search history.

(56) References Cited

U.S. PATENT DOCUMENTS

| | | | | |
|---|---|---|---|---|
| 4,817,125 A * | | 3/1989 | Sklebitz | A61B 6/06 348/E5.086 |
| 4,897,861 A * | | 1/1990 | Schaefer | A61B 6/06 378/150 |
| 5,048,067 A * | | 9/1991 | Horbaschek | G06T 5/50 378/156 |
| 5,107,529 A * | | 4/1992 | Boone | A61B 6/4035 359/890 |
| 5,170,425 A * | | 12/1992 | Haendle | H04N 5/32 348/E5.086 |
| 5,278,887 A | | 1/1994 | Chiu et al. | |
| 5,282,254 A * | | 1/1994 | Chiu | A61B 6/06 378/159 |
| 5,369,678 A * | | 11/1994 | Chiu | A61B 6/06 378/152 |
| 5,923,724 A * | | 7/1999 | Soukal | A61B 6/06 348/E5.088 |
| 6,036,362 A * | | 3/2000 | Schmitt | A61B 6/08 378/150 |
| 6,094,474 A * | | 7/2000 | Vezina | G21K 1/10 378/156 |
| 6,101,238 A * | | 8/2000 | Murthy | G01N 23/04 378/62 |
| 6,330,299 B1 * | | 12/2001 | Curtis | G01N 23/04 378/108 |
| 6,463,121 B1 * | | 10/2002 | Milnes | A61B 6/4482 378/62 |
| 6,501,828 B1 * | | 12/2002 | Popescu | A61B 6/06 378/145 |
| 6,563,909 B2 * | | 5/2003 | Schmitz | A61B 6/032 378/145 |
| 6,735,273 B2 * | | 5/2004 | Flohr | A61B 6/032 378/158 |
| 6,940,948 B1 * | | 9/2005 | Tretiakov | A61B 6/00 378/146 |
| 6,944,269 B2 * | | 9/2005 | Schmitt | A61B 6/08 378/115 |
| 7,110,497 B2 | | 9/2006 | Halsmer et al. | |
| 7,120,231 B2 * | | 10/2006 | Spahn | A61B 6/06 378/151 |
| 7,245,691 B2 * | | 7/2007 | Kiyono | A61B 6/032 378/4 |
| 7,272,208 B2 * | | 9/2007 | Yatsenko | A61B 6/032 378/145 |
| 7,340,033 B2 * | | 3/2008 | Mollus | A61B 6/06 378/147 |
| 7,344,305 B2 * | | 3/2008 | Kuzmanovic | A61B 6/08 378/205 |
| 7,356,123 B2 * | | 4/2008 | Mollus | A61B 6/06 348/E5.086 |
| 7,433,503 B2 * | | 10/2008 | Cherek | A61B 5/0555 378/4 |
| 7,522,701 B2 * | | 4/2009 | Jensen | A61B 6/481 378/162 |
| 7,549,798 B2 * | | 6/2009 | Watanabe | A61B 6/4405 378/189 |
| 7,564,038 B2 * | | 7/2009 | Endo | H04N 5/32 250/370.11 |
| 7,715,521 B2 * | | 5/2010 | Sakaida | A61B 6/488 378/8 |
| 7,724,874 B2 * | | 5/2010 | Kameshima | G01T 1/2018 250/370.09 |
| 7,734,007 B2 * | | 6/2010 | Kargar | A61B 6/06 378/196 |
| 7,869,637 B2 * | | 1/2011 | Baumgart | A61B 6/06 382/128 |
| 8,396,184 B2 * | | 3/2013 | Shinno | A61B 6/469 378/5 |
| 8,605,861 B2 * | | 12/2013 | Sipiorski | A61B 6/06 378/98.7 |
| 8,956,044 B2 * | | 2/2015 | Hummel | A61B 6/542 378/205 |
| 8,971,493 B2 * | | 3/2015 | Zhang | A61B 5/7285 378/150 |
| 8,977,015 B2 * | | 3/2015 | Böhm | A61B 6/06 382/128 |
| 9,008,267 B2 * | | 4/2015 | Roberts | A61B 6/06 378/150 |
| 9,078,620 B2 * | | 7/2015 | Shin | A61B 6/4452 |
| 9,109,998 B2 * | | 8/2015 | Nathaniel | G01N 23/04 |
| 9,121,809 B2 * | | 9/2015 | Cox | G01N 23/04 |
| 9,149,247 B2 * | | 10/2015 | Lee | A61B 6/469 |
| 9,254,109 B2 * | | 2/2016 | Becker | A61B 6/544 |
| 9,259,200 B2 * | | 2/2016 | Mountney | A61B 6/12 |
| 9,375,192 B2 * | | 6/2016 | Schildkraut | A61B 6/032 |
| 9,462,985 B2 * | | 10/2016 | Hu | A61B 6/4452 |
| 9,480,443 B2 * | | 11/2016 | Feuerlein | A61B 6/4035 |
| 9,545,234 B2 * | | 1/2017 | Bernhardt | A61B 6/4035 |
| 9,610,053 B2 * | | 4/2017 | Okuno | A61B 6/40 |
| 9,649,086 B2 * | | 5/2017 | Tajima | A61B 6/563 |
| 9,697,923 B2 * | | 7/2017 | Tsuji | A61B 6/4266 |
| 9,700,270 B2 * | | 7/2017 | Tateishi | A61B 6/4266 |
| 9,700,277 B2 * | | 7/2017 | Okuno | A61B 6/06 |
| 9,814,435 B2 * | | 11/2017 | Kim | A61B 6/469 |
| 9,820,705 B2 * | | 11/2017 | Kim | A61B 6/08 |
| 9,820,709 B2 * | | 11/2017 | Melman | A61B 6/469 |
| 9,848,840 B2 * | | 12/2017 | Ohashi | A61B 6/06 |
| 9,861,329 B2 * | | 1/2018 | Shin | A61B 6/5205 |
| 9,931,087 B2 * | | 4/2018 | Melman | A61B 6/585 |
| 9,936,926 B2 * | | 4/2018 | Eronen | A61B 6/06 |
| 9,949,707 B2 * | | 4/2018 | Miyachi | A61B 6/5241 |
| 9,968,311 B2 * | | 5/2018 | Tagawa | A61B 6/4266 |
| 10,034,643 B2 * | | 7/2018 | Kim | A61B 6/469 |
| 10,058,294 B2 * | | 8/2018 | Tagawa | A61B 6/4266 |
| 10,058,299 B2 * | | 8/2018 | Tagawa | A61B 6/463 |
| 10,085,710 B2 * | | 10/2018 | Suzuki | A61B 6/4266 |
| 10,098,598 B2 * | | 10/2018 | Lee | A61B 6/465 |
| 10,104,311 B2 * | | 10/2018 | Takekoshi | G06T 7/0012 |
| 10,123,756 B2 * | | 11/2018 | Karch | G21K 1/10 |
| 10,149,654 B2 * | | 12/2018 | Melman | A61B 6/4441 |
| 10,149,656 B2 * | | 12/2018 | Takagi | A61B 6/505 |
| 10,182,774 B2 * | | 1/2019 | Kappler | A61B 6/542 |
| 10,285,662 B2 * | | 5/2019 | Nekovar | A61B 6/5288 |
| 10,327,717 B2 * | | 6/2019 | Melman | A61B 6/486 |
| 10,420,524 B2 * | | 9/2019 | Yamada | A61B 6/4266 |
| 10,517,547 B2 * | | 12/2019 | Raupach | G21K 1/04 |
| 10,540,764 B2 * | | 1/2020 | Tsukagoshi | A61B 6/032 |
| 10,548,539 B2 * | | 2/2020 | Izumo | A61B 6/468 |
| 10,582,901 B2 * | | 3/2020 | Ivanov | A61B 6/10 |
| 10,638,993 B2 * | | 5/2020 | Yun | A61B 6/467 |

(56) References Cited

U.S. PATENT DOCUMENTS

| | | |
|---|---|---|
| 10,667,767 B2 * | 6/2020 | Stevens .............. A61B 6/4035 |
| 10,702,229 B2 * | 7/2020 | Lee ..................... A61B 6/587 |
| 10,709,396 B2 * | 7/2020 | Lou ..................... A61B 6/032 |
| 10,722,190 B2 * | 7/2020 | Badal-Soler ............ A61B 6/06 |
| 2008/0013686 A1 | 1/2008 | Kameshima et al. |
| 2008/0083876 A1 | 4/2008 | Endo et al. |
| 2008/0095324 A1 | 4/2008 | Watanabe |
| 2013/0272504 A1 | 10/2013 | Deutsch |
| 2014/0219420 A1 | 8/2014 | Ishikawa et al. |
| 2016/0058403 A1 | 3/2016 | Kim et al. |

FOREIGN PATENT DOCUMENTS

| | | |
|---|---|---|
| CN | 101164497 A | 4/2008 |
| EP | 1484016 A1 | 12/2004 |
| EP | 1484017 A1 | 12/2004 |
| WO | 9615722 A1 | 5/1996 |

OTHER PUBLICATIONS

Labbe, Michael, et al., "The x-ray fovea, a device for reducing x-ray dose in fluoroscopy", Medical Physics 21, pp. 471-481; 1994.

* cited by examiner

DEVICE AND METHOD FOR CREATING A PANORAMIC X-RAY RECORDING USING A FIRST SEMI-TRANSPARENT X-RAY SCREEN AND A SECOND SEMI-TRANSPARENT X-RAY SCREEN

CROSS-REFERENCE TO RELATED APPLICATION

This application claims the priority, under 35 U.S.C. § 119, of German patent application DE 10 2016 205 176.8, filed Mar. 30, 2016; the prior application is herewith incorporated by reference in its entirety.

BACKGROUND OF THE INVENTION

Field of the Invention

The invention relates to a device and a method for composing an overview or panoramic x-ray recording consisting of a plurality of individual x-ray images.

X-ray images can be created to assist with medical diagnosis, for instance. Inter alia vascular and bone structures as well as alignments of the spinal column or the legs can be visualized with the x-ray images. Long bones, the entire spinal column or also the representation of a leg with the hip joint including the femur, the knee and the ankle joint can only be determined with difficulty with an individual x-ray image, e.g. in order to determine a leg axis, due to a detector size which limits the x-ray image size. In order to obtain an overall view of the spinal column, a leg or an arm, for instance, a plurality of x-ray images to be arranged in series with one another, also referred to below as partial x-ray images, of the body section to be viewed are created. In order to create an overall image, in each case overlapping areas in the partial x-ray images which are to be joined together are provided so that corresponding distinctive structures can be joined together in the overlapping areas of the adjacent partial x-ray images. If these distinctive structures are only present to a limited extent, correlation methods can be used to calculate correspondences and the adjacent x-ray images are aligned with respect to one another. In order for instance to perform correlation methods successfully, suitably large overlapping areas must be available, however. Wide overlapping areas are however disadvantageous for the patient in that he/she is exposed to an increased x-ray dose. Furthermore, more complicated, time-consuming computing operations are required in order to establish the likelihood of correspondence in the overlapping image parts.

SUMMARY OF THE INVENTION

It is accordingly an object of the invention to provide a method and a device for generating panoramic x-rays which overcomes the above-mentioned and other disadvantages of the heretofore-known devices and methods of this general type and which provides for the creation of a panoramic x-ray recording assembled from partial x-ray images.

With the foregoing and other objects in view there is provided, in accordance with the invention, an x-ray device for generating panoramic x-ray images, comprising:

an x-ray source configured to output an x-ray beam cone and a detector for creating partial x-ray images;

the x-ray source having an x-ray screen unit with a first semi-transparent x-ray screen and/or a second semi-transparent x-ray screen to be actuated for taking partial x-ray images of a panoramic x-ray image;

the first semi-transparent x-ray screen and/or the second semi-transparent x-ray screen being disposed for movement into the x-ray beam cone of the x-ray source to thereby cause at least portions of respectively overlapping areas of the partial x-ray images to be joined to one another to be created with a reduced x-ray dose.

The device and the associated method have an x-ray system for creating partial x-ray images for a panoramic x-ray recording. This x-ray system is equipped with an x-ray screen unit having a first semi-transparent x-ray screen and/or a second semi-transparent x-ray screen. When partial x-ray images are created for a panoramic x-ray recording, the first semi-transparent x-ray screen and/or the second semi-transparent x-ray screen can be actuated such that the first semi-transparent x-ray screen and/or the second semi-transparent x-ray screen are moved into the x-ray beam cone coming from the x-ray source such that at least parts of the overlapping areas of the partial x-ray images to be joined together can be created using a reduced x-ray dose.

The invention is advantageous in that the patient's exposure to x-ray radiation required to create a panoramic x-ray recording is reduced to a significant degree.

The invention is advantageous in that the panoramic x-ray recording can be created rapidly, precisely and in a reproducible manner.

The invention is advantageous in that the overlapping parts of adjacent partial x-ray images can be created using a significantly reduced x-ray dose and areas with high diagnostic reliability can be created using an x-ray dose which is optimized for this purpose.

The invention is advantageous in that the individual partial x-ray images can be joined together without any visible transitions.

The invention is advantageous in that the alignment of the individual partial x-ray images of a panoramic x-ray recording is carried out on the basis of features in parallax-free areas in the individual partial x-ray images.

With the above and other objects in view there is also provided, in accordance with the invention, a method of generating x-ray recordings, the method comprising:

outputting a beam cone with an x-ray source and detecting x-rays with a detector;

creating partial x-ray images for a panoramic x-ray recording and thereby moving a first semi-transparent x-ray screen and/or a second semi-transparent x-ray screen into the x-ray beam cone issuing from the x-ray source such that at least parts of overlapping areas of the partial x-ray images to be joined to one another are created using a reduced x-ray dose.

Other features which are considered as characteristic for the invention are set forth in the appended claims.

Although the invention is illustrated and described herein as embodied in a device and method for creating a panoramic x-ray recording, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

By means of the device and the associated method, during the creation of a panoramic x-ray recording, the use of semi-transparent x-ray screens allows the patient's x-ray exposure to be reduced when partial x-ray images are created, in spite of relatively large overlapping areas.

Figure 1:
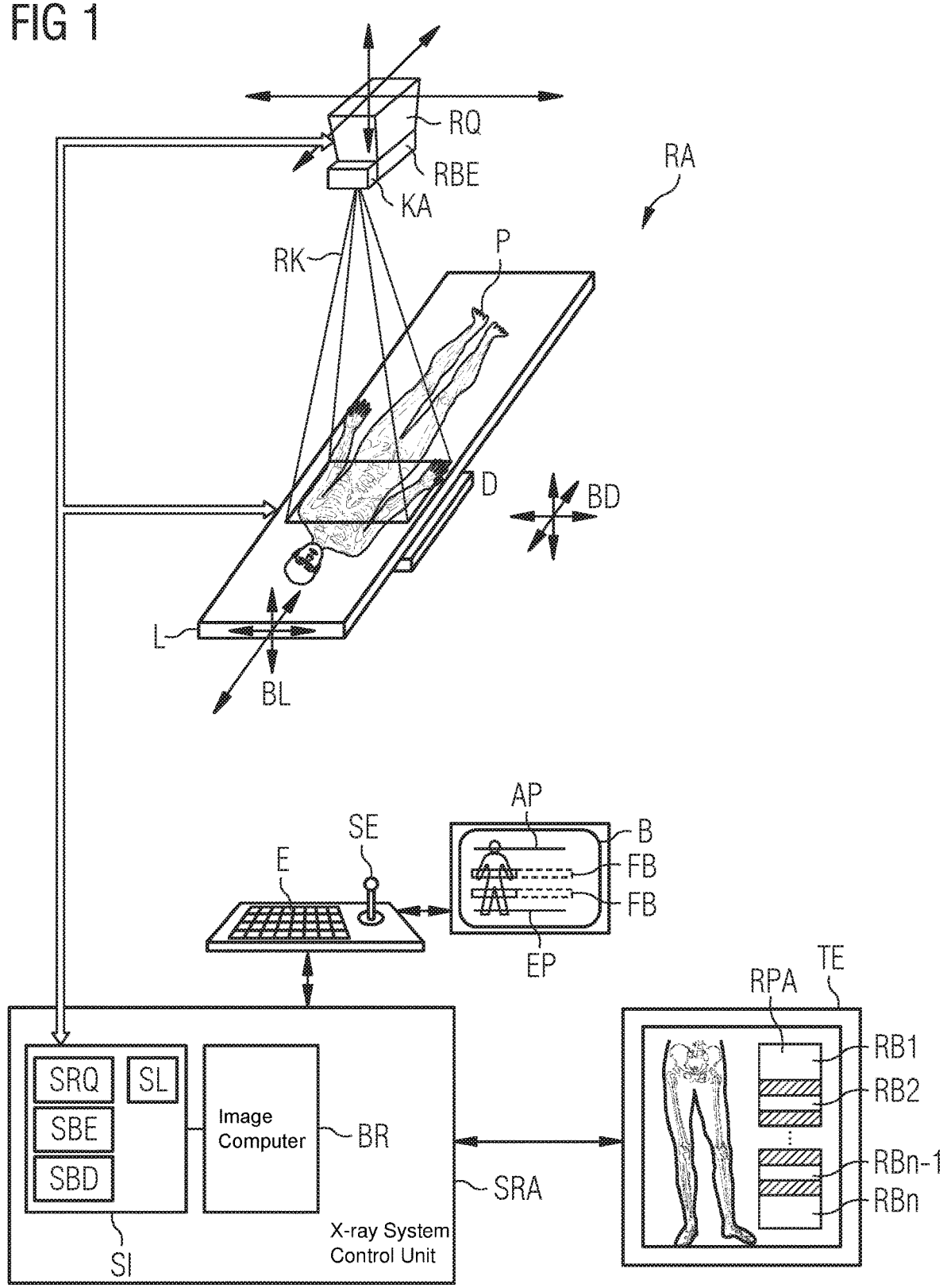
FIG. 1 shows a schematic and diagrammatic view of the arrangement of an x-ray system according to the invention.

Referring now to the figures of the drawing in detail and first, particularly, to FIG. 1 thereof, there is shown a simplified x-ray system RA. The representation schematically shows a patient P positioned on a patient table, or table L. A panoramic x-ray recording of this patient P from the hip and including the legs is to be created for instance. An x-ray source RQ with an x-ray screen unit RBE is arranged above the table L and a detector D is arranged below the table L. A recording unit, for instance a camera KA, is fastened to the x-ray screen unit RBE. In the case of a rigid connection between the x-ray source RQ and detector D, this arrangement is normally moved along the patient P using ceiling or floor supports in order to create a panoramic x-ray recording RPA. In the case of a static arrangement of the x-ray source RQ and detector D, the patient table L can be moved with the patient P positioned thereupon. The directions of movement of the individual components are indicated. With stand-alone systems with, in each case, individual guidance systems for the x-ray source RQ and the detector D, these can be attuned to one another and the x-ray source RQ and the detector D can be moved in alignment with one another along the patient P. Combined or corresponding movements between the x-ray source RQ, detector D, table L are likewise possible in order to create a panoramic x-ray recording RPA of the patient P.

The respective positions of the x-ray source RQ, detector D and table L and patient P are known inter alia to the image computer BR so as to create the overview recording or the panoramic x-ray recording RPA. The individual components represented here such as x-ray source RQ, x-ray screen unit RBE, camera KA, detector D, table L and patient P are configured such that their positions are forwarded to the x-ray system control unit SRA with each x-ray image or partial x-ray image for a panoramic x-ray recording. The image computer BR arranged in the x-ray system control unit SRA can access this position data. The alignment or the movement of the individual components such as x-ray source RQ, detector D or possibly table L can be carried out using a control unit SE assigned to an input unit E. Inter alia individual processor-controlled control units such as an x-ray control unit SRQ, a screen control unit SBE, a detector control unit SBD and a table control unit SL are arranged in the x-ray system control unit SRA.

The x-ray source RQ is controlled in a coordinated manner with the other components of the x-ray system RA by way of an x-ray source control unit SRQ arranged in the x-ray system control unit SRA. The x-ray screen unit RBE can be actuated by way of the screen control unit SBE such that at least one first and/or second semi-transparent x-ray screen ERB, ZRB within the x-ray screen unit RBE can be actuated such that these can be moved into the x-ray beam cone RK coming from the x-ray source RQ in accordance with the position of a partial x-ray image RB1, . . . , RBn within the panoramic x-ray recording RPA.

Figure 2:
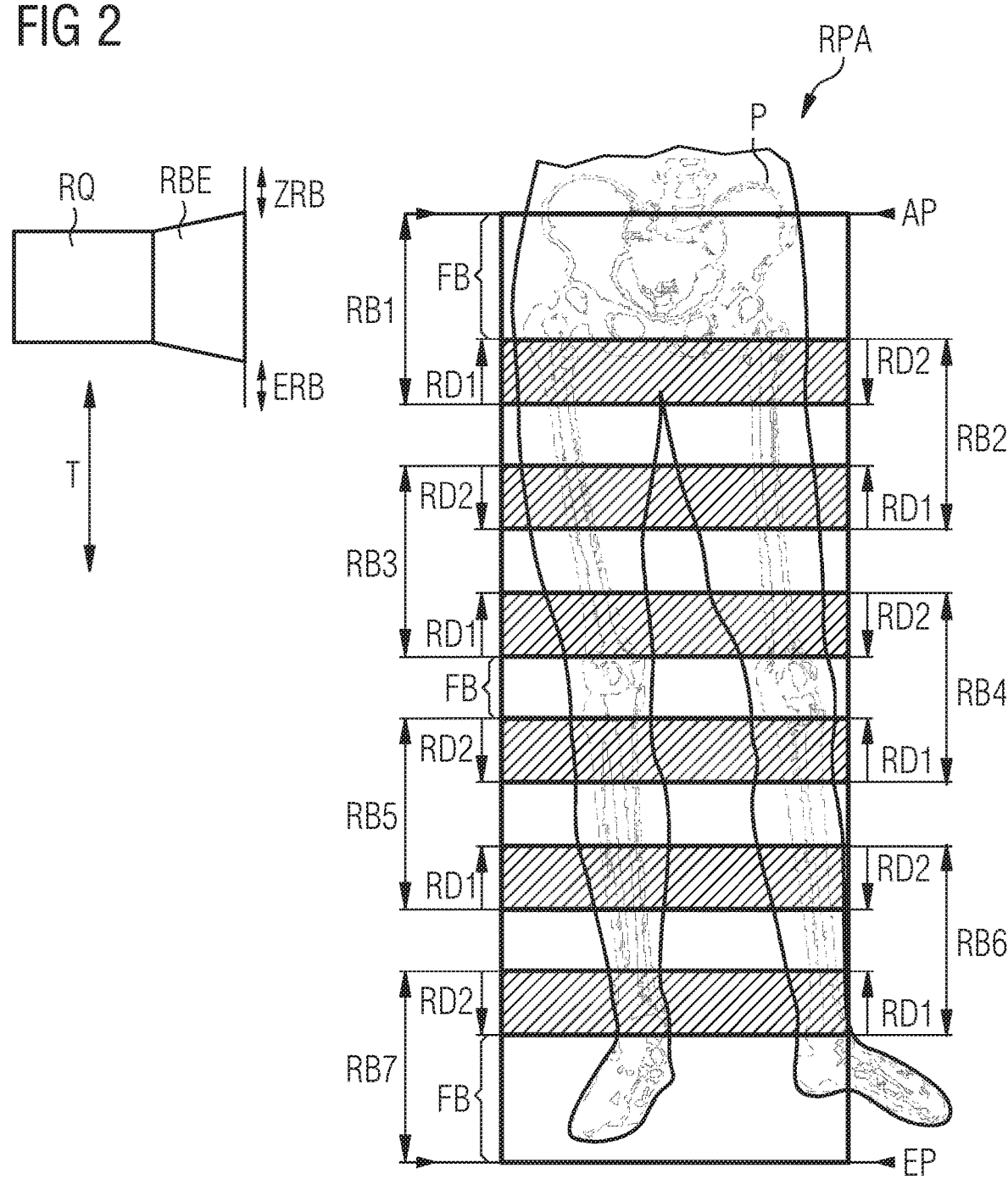
FIG. 2 is a schematic illustrating the formation of a first panoramic x-ray recording.
Figure 3:
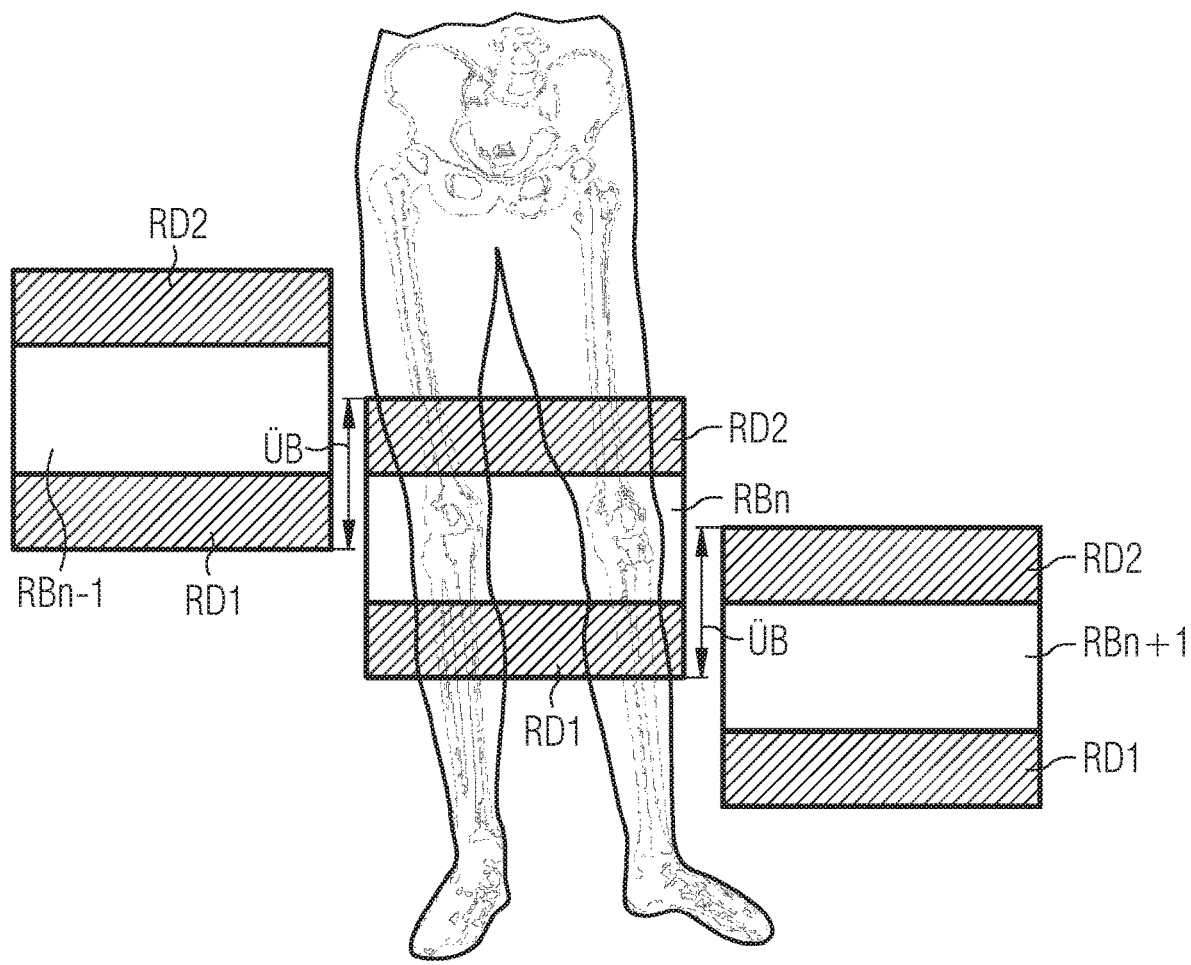
FIG. 3 is a similar view illustrating the formation of a second panoramic x-ray recording.

A panoramic x-ray recording RPA can be composed here, as shown in FIG. 3 or FIG. 2, with partial x-ray images RB1, . . . , RBn using a uniform or varying x-ray dose, in particular in the overlapping areas. The input unit E can be used to create a panoramic x-ray recording RPA in a menu-controlled manner, for instance indicated on a monitor B or by way of input assistance from a touchscreen unit TE. A first boundary line AP for the beginning and a second boundary line EP for the end of the panoramic x-ray recording RPA is entered onto the monitor B or the touchscreen unit TE on a patient P. The patient P may be represented schematically or by way of a video camera. In addition, so-called focus areas FB can be defined, in which the respective partial x-ray image RBx is to be created with a best-possible x-ray image quality. The image computer BR arranged in the x-ray system control unit SRA then determines the number of partial x-ray images RB1, . . . , RBn between the first boundary line AP and the second boundary line, EP by taking focus areas FB into account when a selectable detector D of a certain size is used. The width of the possible overlapping areas OL of the boundary areas of the partial x-ray images RB1, . . . , RBn to be overlaid on to one another can likewise be predefined. Subsequently, by means of inputting it is determined whether the panoramic x-ray recording RPA is to be created with a constant x-ray image quality or with a varying x-ray image quality. In order to significantly reduce the x-ray load exposure for the patient P, a first semi-transparent x-ray screen ERB and/or a second semi-transparent x-ray screen, ZRB, at least in the overlapping areas, is moved into the x-ray beam cone RK coming from the x-ray source RBE. If a panoramic x-ray recording RPA with a varying x-ray image quality is to be compiled, a narrower overlapping area OL can be predefined and this can be covered in each case by the first semi-transparent x-ray screen ERB and/or the second semi-transparent x-ray screen, ZRB. If a panoramic x-ray recording RPA is to be formed with a constant x-ray image quality, a large overlapping area OL is predetermined and a semi-transparent x-ray screen ERB, ZRB only covers half of the respective overlapping area OL of the partial x-ray images RB1, . . . , RBn to be joined together for instance.

FIG. 2 shows a first embodiment variant for creating a panoramic x-ray recording RPA. The x-ray source RQ is moved along a trajectory T. The objective here is to capture the hip and legs of the patient P with this panoramic x-ray recording RPA. The beginning of the panoramic x-ray recording RPA is marked with a first boundary line AP on the upper edge of the hip and the end of the panoramic x-ray recording RPA with a second boundary line EP below the ankle joint. For the sake of clarity, only the x-ray source RQ and an x-ray screen unit RBE arranged downstream of the x-ray source RQ is indicated here. At the exit of the x-ray screen unit RBE, a first semi-transparent x-ray screen ERB and a second semi-transparent x-ray screen ZRB in the screen opening of the x-ray screen unit RBE, depending on the requirement, can be moved into the x-ray beam cone RK output by the x-ray source RQ. How far the first semi-transparent x-ray screen and the second semi-transparent x-ray screen ERB, ZRB, in each case, is pushed or moved into the partial x-ray images RB1, . . . , RBn to be created can be predetermined before beginning the panoramic x-ray recording RPA by specifying a first overlapping area RD1 and a second overlapping area RD2. If for instance a partial x-ray image RB1 representing the hip area of the patient is begun, the first semi-transparent x-ray screen ERB in the x-ray screen unit RBE is moved into the x-ray beam cone RK by the x-ray source RQ after the size of a first overlapping area RD1 has been predetermined. For a second partial x-ray image RB2, the x-ray source RQ is moved accordingly along the trajectory T. During the movement of the x-ray source RQ, the second semi-transparent x-ray screen ZRB is moved into the opening of the x-ray screen unit RBE. The second partial x-ray image RB2 begins where the first overlapping area RD1 in the first partial x-ray image RB1 begins. Contrary to the first partial x-ray image RB1, the second partial x-ray image RB2 has a first overlapping area RD1 and a second overlapping area RD2. Within these first and second overlapping areas RD1, RD2, the x-ray dose of the x-ray beams directed at the patient P is reduced in accordance with the semi-transparent x-ray screens ERB, ZRB used. The width of the second overlapping area RD2 generated by the second semi-transparent x-ray screen ZRB in the second partial x-ray image RB2 corresponds to the width of the first overlapping area RD1 in the first partial x-ray image RB1 recorded with a reduced x-ray dose. Subsequent partial x-ray images RB3, . . . RBn−1 are created in the same way. The area between the first and second transition area RD1, RD2 in the partial x-ray images is x-rayed in each case with an x-ray dose optimized to the respective object section. The creation of further overlapping partial x-ray images RBn for the panoramic x-ray recording RPA is continued up to the second boundary line EP. However, with the last partial x-ray image RB7 for the panoramic x-ray recording RPA, the first semi-transparent x-ray screen ERB is moved out of the x-ray screen unit RBE, since only one more overlapping area for the preceding partial x-ray image RB6 is required. In the overall image a panoramic x-ray recording RPA, which could be created in the form of strips, is produced. This panoramic x-ray recording RPA then has areas with a high-contrast representation between the respectively overlapping first and second overlapping areas RD1, RD2. The partial x-ray images RB2, RB3, RB5 and RB6 in which neither hip joints, knee or ankle joints are represented can be created using a lower x-ray dose. This composition of the panoramic x-ray recording RPA is advantageous in that at least areas near the leg, such as for instance the socket of the pelvis, the knee and the ankle joint of the foot, were defined as focus areas FB and are represented with optimized x-ray radiation in the partial x-ray images RB1, RB4 and RB7. The long bones in between are of less importance in terms of assessing or establishing a leg axis for instance. In these sections, the patient P is only exposed here to a reduced x-ray dose.

FIG. 3 shows a further exemplary embodiment for assembling a first, second and third partial x-ray image RBn−1, RBn, RBn+1 to form a panoramic x-ray recording RPA. In this exemplary embodiment, contrary to the exemplary embodiment under FIG. 2, larger overlapping areas OL are provided in each case for the partial x-ray images. These overlapping areas OL between two partial x-ray images have at least the width of the first and/or second areas RD1, RD2 generated by the first and second x-ray screens ERB, ZRB in the corresponding partial x-ray images. If an adjacent partial x-ray image RBx−1 is joined to a partial x-ray image RBx and/or RBn+1 to form a panoramic x-ray recording RPA, the overlapping areas OL between the partial x-ray images RBx−1, RBx and RBx+1 are placed one on top of the other. When assembling partial x-ray images RB1, RB2; RP2, RP3; . . . , RBn, RBn+1, in each case the overlapping area OL extends approximately as far as the center of the partial x-ray images for instance. A section of a partial x-ray image with an object-related x-ray irradiation and an area of the partial x-ray image in which the x-ray radiation was reduced by the use of a first semi-transparent x-ray screen ERB or a second semi-transparent x-ray screen ZRB, lie one on top of the other in the overlapping areas in each case. If the overlapping area OL between the second and third partial x-ray image RBn, RBn+1 is viewed for instance, a section with an optimized x-ray radiation from the second partial x-ray image RBn with the second area RD2, the third partial x-ray image RBn+1 and the first area RD1 from the second partial x-ray image RBn with a section of the third partial x-ray image RBn+1 lie one above the other. An alignment of the second and third partial x-ray image RBn, RBn+1 and an alignment of the first and second partial x-ray image RBn−1, RBn is carried out in each case with the aid of identical distinctive points or surface structures in the overlapping areas OL. On completion of the correlation between the respectively adjacent partial x-ray images RB1, . . . , RBn, the areas which were recorded with a reduced x-ray dose are separated from the respective partial x-ray images and the remaining parts of the partial x-ray images RBn−1, RBn, RBn+1 are joined in a transition-free manner with one another.

In a further embodiment variant, only one boundary area per partial x-ray image, for instance an area which was recorded through a first x-ray screen ERB with a reduced x-ray dose RD1, can be overlaid with a boundary area of an adjacent partial x-ray image.

The following is a summary list of reference numerals and the corresponding structure used in the above description of the invention:

| | |
|---|---|
| T | Trajectory |
| RA | X-ray system |
| KA | Camera |
| RQ | X-ray source |
| RK | X-ray beam cone |
| RBE | X-ray screen unit |
| D | Detector unit |
| L | Table, patient table |
| P | Patient |
| BD | Detector movement direction |
| BL | Table movement direction |
| SRA | X-ray system control unit |
| S | Control unit |
| SL | Table control unit |
| SRQ | X-ray source control unit |
| SBE | X-ray screen control unit |
| SBD | Detector control unit |
| BR | Image computer |
| SE | Joystick |
| E | Input unit |
| TE | Touchscreen unit, display |
| RB1, . . . , RBn | First, . . . , n$^{th}$ partial x-ray image (RBn − x, . . . , RBn, . . . , RBn + y) |
| ERB | First semi-transparent x-ray screen/collimator |
| ZRB | Second semi-transparent x-ray screen/collimator |
| DA1, . . . , DAx | Detector representations |
| RPA | Panoramic x-ray recording |
| OL | Overlapping area |
| B | Monitor unit, display |
| AP | First boundary line |
| EP | Second boundary line |
| FB | Focus areas |
| RD1 | First overlapping area |
| RD2 | Second overlapping area |

The invention claimed is:

1. An x-ray device for generating panoramic x-ray images, comprising:
an x-ray source configured to output an x-ray beam cone; and
a detector for creating partial x-ray images;
said x-ray source having an x-ray screen unit with a first semi-transparent x-ray screen and/or a second semi-transparent x-ray screen to be actuated for taking partial x-ray images of a panoramic x-ray image;

said first semi-transparent x-ray screen and/or said second semi-transparent x-ray screen being disposed for a movement into the x-ray beam cone of said x-ray source to thereby cause at least portions of respectively overlapping areas of the partial x-ray images to be joined to one another to be created with a reduced x-ray dose; and a control system configured to define an overlap width of the overlapping areas of the partial x-ray images and to compose a panoramic x-ray image by joining the partial x-ray images to one another and respectively overlapping one another in the overlapping areas.

2. The x-ray device according to claim 1, further comprising a monitor and an input unit configured to enable a first boundary line and a second boundary line to be marked on a patient who is being displayed on said monitor.

3. The x-ray device according to claim 2, wherein said input unit allows at least one focus area to be predetermined.

4. The x-ray device according to claim 1, further comprising a camera disposed to record a patient and an image computer configured to enable a segmentation of the partial x-ray images for a panoramic x-ray image to be specified with an aid of said camera.

5. An x-ray device for generating panoramic x-ray images, comprising:

an x-ray source configured to output an x-ray beam cone; and a detector for creating partial x-ray images;

said x-ray source having an x-ray screen unit with a first semi-transparent x-ray screen and/or a second semi-transparent x-ray screen to be actuated for taking partial x-ray images of a panoramic x-ray image;

said first semi-transparent x-ray screen and/or said second semi-transparent x-ray screen being disposed for a movement into the x-ray beam cone of said x-ray source to thereby cause at least portions of respectively overlapping areas of the partial x-ray images to be joined to one another to be created with a reduced x-ray dose;

a camera disposed to record a patient; and an image computer configured to enable a segmentation of the partial x-ray images for a panoramic x-ray image to be specified with an aid of said camera.

6. A method of generating x-ray recordings, the method comprising:

providing an x-ray source with a first semi-transparent x-ray screen and a second semi-transparent x-ray screen;

outputting an x-ray beam cone with the x-ray source;

detecting x-rays with a detector;

creating partial x-ray images by moving the first semi-transparent x-ray screen and/or the second semi-transparent x-ray screen into the x-ray beam cone output from the x-ray source such that at least parts of overlapping areas of the partial x-ray images to be joined to one another are created using a reduced x-ray dose; and creating a panoramic x-ray image by joining the partial x-ray images to one another with areas of adjoining partial x-ray images that are created with the reduced x-ray dose overlapping one another.

7. The method according to claim 6, further comprising displaying a patient on a monitor and enabling a first boundary line and a second boundary line to be marked on the patient represented on the monitor.

8. The method according to claim 7, further comprising specifying at least one focus area.

9. The method according to claim 7, further comprising predetermining a width of an overlapping area between two adjoining partial x-ray images.

10. The method according to claim 6, further comprising creating a segmentation of the partial x-ray images for a panoramic x-ray image on a basis of a camera recording the patient.

* * * * *